United States Patent [19]

Clemons

[11] Patent Number: 5,625,035
[45] Date of Patent: Apr. 29, 1997

[54] ERYTHROPOIETIN BINDING PROTEIN FROM MAMMALIAN SERUM

[75] Inventor: Gisela K. Clemons, Berkeley, Calif.

[73] Assignee: The Regents, University of California, Oakland, Calif.

[21] Appl. No.: 202,717

[22] Filed: Feb. 23, 1994

Related U.S. Application Data

[63] Continuation of Ser. No. 893,733, Jun. 5, 1992, abandoned.

[51] Int. Cl.$^6$ .............................. C07K 2/00; C07K 14/43; C07K 14/505; A61K 38/02
[52] U.S. Cl. ..................... 530/380; 530/350; 530/351; 530/395; 530/397; 530/402; 530/391.7; 435/174
[58] Field of Search .................................. 530/380, 350, 530/351, 395, 397, 402, 391.7; 435/174; 514/2, 8

[56] References Cited

U.S. PATENT DOCUMENTS

| | | | |
|---|---|---|---|
| 4,558,006 | 12/1985 | Egrie | 435/7 |
| 5,378,808 | 1/1995 | D'Andrea et al. | 530/350 |

OTHER PUBLICATIONS

D'Andrea, A. D., et al., (1989) Cell 57: 277–85.
Blum, W.F., et al., (1989) Endocrinol. 125: 766–792.
Todokero, et al. (Oct. 5, 1991) Gene 106: 283–4.
Metzler, D.M. (1977) *Biochemistry*, New York: Academic Press, p. 374.
Takahashi, T., et al. (1995) *Blood* 85(1): 106–114.
J. Garcia and G. Clemons, *Recent Advances in Nuclear Medicine*, The Radioimmunoassay of Erychropoietin, vol. 6, pp. 19–31, (1983).
A. Besarab, *Am. J. Nephrol*, Recombinant Human Erythropoietin: Physiology of Anemia in Renal Failure and Economic Aspects Related to Dosing, 10 (suppl 2) pp. 2–6, (1990).
B. Varet, N. Casadevall, C. Lacombe, P. Nayeaux, Erythropoeitin: Physiology and Clinical Experience, *Seminars in Hematology*, vol. 27: (Suppl. 3), pp. 25–31, (Jul. 1990).

D. Bowen, B. Ehmer, P. Neubert, T. Lewis, and A. Jacobs, The Clearance of a Single i.v., Bolus of Recombinant Human Erythropoeitin from the Serum of Patients with Myelodysplastic Syndromes and Its Effects on Erythropoiesis, *Experimental Hematology*, 19:613–616 (1991).

R. Abels and S. Rudrick, Erythropoietin: Evolving Clinical Applications, *Experimental Hematology*: 19:842–850 (1991).

J. George, C. Bracco, K. Shannon, G. Davis, L. Smith, R. Phibbs, and A. Hendrickx, Age–Related Differences in Erythropoietic Response to Recombinant Human Erythropoietin: Comparison in Adult and Infant Rhesus Monkeys *Pediatric Research*, vol. 28:6, pp. 567–571, (1990).

K. Shannon, Recombinant Erythopoietin in Pediatrics: A Clinical Perspective, *Pediatric Annals*, 19:197–206 (1990).

J. Eschbach and J. Adamson, Recombinant Human Erythropoietin: Implications for Nephrology, *American Journal of Kidney Diseases*, vol. 11:3, pp. 203–209, (Mar. 1988).

*Primary Examiner*—Garnette D. Draper
*Assistant Examiner*—David L. Fitzgerald
*Attorney, Agent, or Firm*—Paul R. Martin; Kathleen Dal Bon; Pepi Ross

[57] ABSTRACT

Purified mammalian erythropoietin binding-protein is disclosed, and its isolation, identification, characterization, purification, and immunoassay are described. The erythropoietin binding protein can be used for regulation of erythropoiesis by regulating levels and half-life of erythropoietin. A diagnostic kit for determination of level of erythropoietin binding protein is also described.

8 Claims, 11 Drawing Sheets
(3 of 11 Drawing(s) in Color)

ERYTHROPOIETIN BINDING PROTEIN FROM MAMMALIAN SERUM

This invention was made with Government support under Contract No. DE-AC03-76SF00098 between the U.S. Department of Energy and the University of California for the operation of Lawrence Berkeley Laboratory and under the National Institute of Health, Lung, and Blood Institute grant HL 22469. The Government has certain rights in this invention.

This is a continuation of prior application Ser. No. 07/893,733, filed 5 Jun. 1992, now abandoned.

BACKGROUND OF THE INVENTION

Field of Invention

This invention concerns erythropoietin binding protein and an assay for its determination. Particularly, this invention concerns the erythropoietin binding protein and its isolation, identification, characterization, and purification, cloning, and expression. The erythropoietin binding protein is useful for regulation of erythropoiesis by regulating levels of erythropoietin via formation of erythropoietin-erythropoietin binding protein complex. Formation of erythropoietin-erythropoietin binding protein complex prolongs the biological activity of erythropoietin and prevents its ultimate depletion by filtration into the urine or by catabolism in liver.

BACKGROUND ART AND RELATED ART DISCLOSURES

Binding proteins for various hormones have been reported in the literature. A highly specific, high affinity, low-capacity binding protein for human growth hormone has been reported in the *J. Clin. Endocrinol. Metab.* [62: 134 (1986)]. The growth hormone binding protein was further identified and characterized in 1988. It has also been reported that a substantial fraction of growth hormone in normal plasma exists as a complex in association with its specific binding protein [*Endocrinology*, 122: 976 (1988)]. The growth hormone binding protein was shown to affect growth hormone homeostasis, its kinetics, and metabolism by modulating its interaction with tissue receptors.

Mechanism of Erythropoietin Activity. Erythropoietin is a glycoprotein hormone which is a principal regulator of erythropoiesis, the production of red blood cells. Erythropoietin enhances erythropoiesis by stimulating formation and proliferation of proerythroblasts into reticulocytes and subsequent release of reticulocytes from bone marrow. Ultimately, erythropoietin stimulates the maturation of reticulocytes into morphologically identifiable red blood cells. After fetal life, erythropoietin is largely produced by kidney in response to tissue hypoxia. Its production, therefore, is principally regulated by the level of renal oxygenation. Approximately 10–15% of erythropoietin is produced by extrarenal sites, including the liver, which seems to be responsible for residual erythropoietin production in anephric patients and in the fetus.

Effects of Erythropoietin Deficiencies. Anemia develops whenever there is a deficiency in erythrocyte count. It develops in response to various causes such as sickling disorders, homozygous beta thalassemia, hereditary spherocytosis, red cell enzymopathies, iron, vitamin $B_{12}$, folate deficiencies, aplastic anemia, Fanconi's anemia, Blackfan Diamond anemia, or leukemia. These disorders are generally accompanied by increased endogenous erythropoietin production. When, however, a patient suffers from acute renal failure or when the chronic renal failure develops, the inadequate renal production of erythropoietin results in hypoplastic anemia. Similarly, anemia in premature infants develops when a progressive fall in hemoglobin concentration, relatively low absolute reticulocyte counts, and bone marrow erythroid hypoplasia develops from low concentration of serum erythropoietin.

The effect of reduced erythropoietin on development of anemia during chronic renal failure has been known and is further substantiated by findings described in *Lancet*, 1175 (1986) and in *N.Engl.J.Med*, 316: 731 (1987), which report that anemia in patients undergoing hemodialysis is completely reversed with recombinant human erythropoietin. These findings suggest that the anemia is due primarily, if not solely, to erythropoietin deficiency, Treatment with Exogenous Erythropoietin. The presence and availability of erythropoietin for regulation of erythropoiesis is of extreme importance for sustenance of the normal physiological state of the human being. When, for any reason, the production, release or levels of erythropoietin in the plasma decrease, there are severe consequences affecting the patient's well being. It is therefore, extremely important that erythropoietin is available or made available to control erythropoiesis even when the production and/or release of erythropoietin is blocked by renal disease or by some other pathological conditions.

Recently, with the advent of recombinant technology, recombinant human erythropoietin has become available for administration to patients with anemia due to renal failure and for treatment of other diseases where the endogenous level of erythropoietin in the serum is low. However, such recombinant human erythropoietin is expensive. Because it is necessary to administer such recombinant human erythropoietin continuously to prevent the recurrence of anemia, the cost of such treatment may be prohibitive.

It would be an important advancement in the treatment of EP deficiency if a means could be developed that would extend the circulation half-life of erythropoietin.

SUMMARY

The inventor has unexpectedly discovered the existence of a naturally occurring erythropoietin binding protein which has many pharmacological, purification, and immunoassay applications. For the first time the functioning of naturally occurring EP can be optimized, in some cases eliminating the need for further treatment of a patient. The inventive purified erythropoietin binding protien is also useful in assaying erythropoietin and in isolating and purifying this hormone.

It is thus an object of the present invention to provide a purified erythropoietin binding protein.

The binding protein will have a molecular weight in the range of from about 90,000 to 100,000 Da, more particularly in the range of from about 92,000 to 97,400 Da. An erythropoietin binding protein of the invention which is exemplified herein has a molecular weight of from about 93,000 Da to 96,000 Da. This protein is capable of forming a complex with erythropoietin, the complex having a molecular weight of from about 125,000 to 135,000 Da. A complex exemplified herein has a molecular weight of about 130,000 Da.

Another object of the present invention is the isolation and purification of an erythropoietin binding protein which can form a complex with erythropoietin, extending the half-life of erythropoietin in plasma.

Still another object of the present invention is to treat or prevent anemia by administering to an anemic person an erythropoietin binding protein alone, or in combination with erythropoietin, to stimulate erythropoiesis.

Yet another object of the present invention is the isolation, identification, characterization, and purification of erythropoietin binding protein.

A further object of the present invention is to provide an immunoassay for determination of concentration in human plasma of erythropoietin binding protein. BRIEF DESCRIPTION OF DRAWINGS The file of this patent contains at least one drawing executed in color. Copies of this patent with color drawing (s) will be provided by the Patent and Trademark Office upon request and payment of the necessary fee.

DETAILED DESCRIPTION OF THE INVENTION

Figure 1:
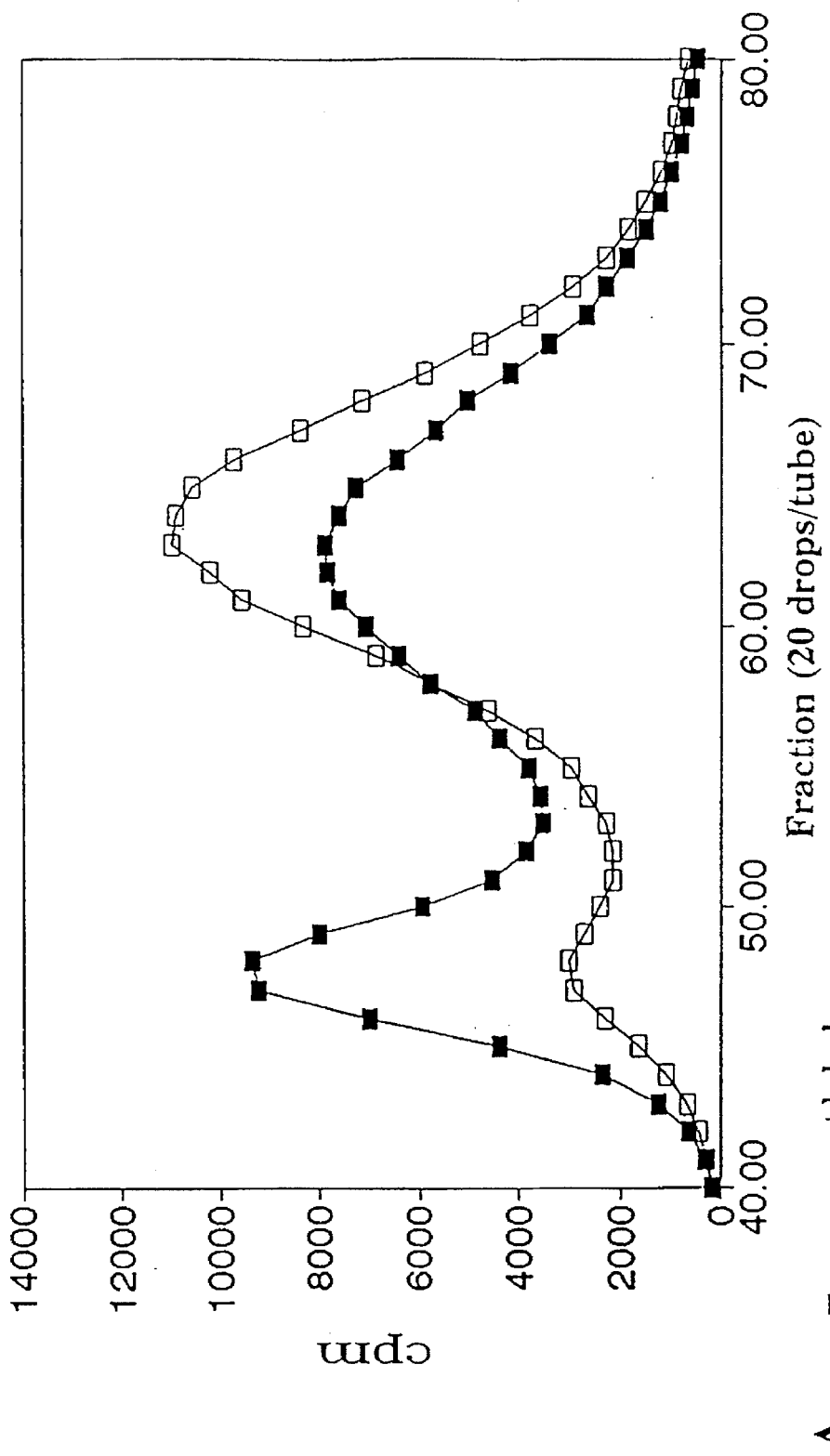
FIG. 1 depicts elution fraction peaks following gel filtration of erythropoietin binding protein complex and free erythropoietin in filtered normal human serum containing labeled and nonlabeled erythropoietin.

The present invention concerns a newly discovered erythropoietin binding protein in the human serum. Other mammalian species will have the same or closely related proteins. These binding proteins form an erythropoietin-erythropoietin binding protein complex with circulating free erythropoietin. In this way, erythropoietin binding protein extends the half-life of circulating erythropoietin. The formation of erythropoietin-erythropoietin binding protein complex prevents rapid excretion by kidney or degradation by liver of free erythropoietin from the blood and, therefore, erythropoietin is able to perform longer its primary function, that is to stimulate formation and maturation of new red blood cells. The binding proteins of the present invention will have important applications in assays and purifications, as well as pharmacology.

Erythropoietin. Erythropoietin can be detected in both plasma serum and urine. Under normal condition, erythropoietin is detectable in plasma serum at an average concentration of approximately 10 to 20 mU/ml. The amount of erythropoietin in the serum varies inversely with the level of tissue oxygenation and is dependent on the feedback provided by the lack of excess of oxygen in the tissue. Thus, serum erythropoietin level rises when there is tissue hypoxia and stimulates production of red blood cells. Increased levels of erythropoietin were observed to be caused by factors such as anemia, right to left cardiac shunting, chronic obstructive pulmonary disease or exposure to high altitudes. When, in response to hypoxia, an increased red cell mass induced by erythropoietin corrects tissue hypoxia, serum erythropoietin levels fall and return to their baseline level.

The physiological importance of erythropoietin stems from its role as erythropoiesis regulator. The cardiovascular and pulmonary systems and circulating erythrocytes function together to deliver oxygen and nutrients throughout the body. The peripheral oxygen delivery in humans is achieved through its binding to hemoglobin of the circulating erythrocytes. The number of circulating erythrocytes is thus decisive for normal health and body function. When, for any reason, either the number of erythrocytes decreases or the demand for oxygen in the peripheral tissue increases, causing the peripheral oxygen deficiency, such oxygen deficiency is sensed by cells in the kidneys which respond by the release of erythropoietin into the circulation. Erythropoietin, in turn, induces proliferation and terminal differentiation of bone marrow erythroid precursors. This ultimately affects the release and maturation of reticulocytes resulting in the larger number of erythrocytes entering the circulation. When the increased number of erythrocytes deliver a larger volume of oxygen into the peripheral tissue, thus decreasing a tissue hypoxia, the kidney cells sense the higher amount of oxygen and cease to further produce or release erythropoietin.

EP Binding Protein in Adults. The inventor postulated protective mechanisms for binding protein in the blood of normal adult person, which provided the motivation for the research effort resulting in the present invention. This theory came from the observation that 1 ml of normal human serum contains between 15–20 mU (100 pg/ml) of erythropoietin. In the serum of a normal human weighing 70 kg who has approximately 5 liters of blood of which 3 liters is serum, there is thus approximately 60,000 mU of total erythropoietin at any given time. The half-life of the erythropoietin in normal adult is reported to be between 6 to 8 hours. If no mechanism exists for extension of erythropoietin half-life in the blood, every eight hours, a half (that is, about 30,000 mU), of the total 60,000 mU is excreted in the urine or inactivated in liver. Therefore, approximately 90,000 mU/24 hours would be expected to be excreted in urine or deactivated in liver from the blood circulation of a normal person. Yet, it has been reported that during 24 hours, only about 4,000 mU of erythropoietin are excreted in the urine.

Under normal circumstances, that is in normal healthy adult, approximately 90% of erythropoietin is produced in the adult kidney and less then 10% is produced by liver. Erythropoietin production occurs in response to the renal hypoxia. Released erythropoietin is needed and used for stimulation of erythropoiesis. Without the presence of the binding protein, the half-life of erythropoietin would be significantly shortened. By binding to its own specific binding protein, the circulation of erythropoietin is substantially extended. It is, therefore, expected that the amount of binding protein would be such as to assure the normal function of erythropoietin. This theory of the inventor has support in current finding that the normal human plasma contains higher amount of binding protein compared to fetal, newborn animal or anephric plasma.

EP Binding Proteins in Neonatal and Renal Patients. During fetal life, the source of erythropoietin production switches from the liver to the kidney during the third trimester of pregnancy. Significantly greater clearances, short half-lives, shorter residence times, greater distribution volumes and greater erythropoietin production rates have been reported in fetuses and neonates compared to adults. These developmental differences reflect greater distribution of erythropoietin and more rapid metabolism in less mature individuals. The rapid metabolism reduces erythropoietin's erythropoietic effectiveness and may be the result of lower concentrations of erythropoietin binding protein. In fact, the level of binding protein in fetal and neonatal plasma was found by the inventor to be about two-thirds of that of normal adult plasma. Prematurely born infants are typically afflicted with the anemia of prematurity. These infants not only have low circulating levels of erythropoietin but also inadequate production of erythropoietin. At birth, the liver production ceases to be sufficient to produce all erythropoietin needed. At the same time, kidney is not immediately able to assume the production of erythropoietin. Therefore, the prematurely born infants are often afflicted with anemia. It has been previously reported and confirmed that the level of erythropoietin in prematurely born infants is only about one-half of that of the normal adult. Attempts to correct these anemias of prematurity using recombinant human erythropoietin doses shown to be effective in adults, have been ineffective in these prematurely born infants and the administration of higher doses was necessary. The lack of efficacy of correcting the anemia of prematurity is indicated by significantly lower levels of erythropoietin binding protein.

Similarly, anephric patients or patients suffering from chronic renal failure develop anemia because of the inadequate renal erythropoietin production. In anephric patients, both the level of circulating erythropoietin and binding protein is very low. The level of erythropoietin binding protein was found to be only about one-third of that observed in the normal adult. Thus, not only these patients have low levels of erythropoietin but they also have a limited mechanism for extension of the erythropoietin half-life.

The premature and chronic renal failure anemias can be treated with recombinant erythropoietin in amounts which will be equal to those found in normal adult. Such treatment is currently been successfully utilized, at least in certain cases of chronic renal failure. However, some patients need higher doses for the same correction of hematocrit, that is for production of sufficient number of red blood cells, than other individuals. Similarly, prematurely born infants respond to treatment with recombinant human erythropoietin only at 2-3 times the adult dose. In both cases, the lack or low levels of binding protein seems indicated and was in fact found.

I. Erythropoietin Binding Protein in Normal Human Serum

The existence of the erythropoietin binding protein can be proven by its specific binding to the erythropoietin. In order to unequivocally prove that there is such a specific binding protein, the formation of the erythropoietin-erythropoietin binding complex must be shown. The complex must have a molecular weight higher than that of erythropoietin. When the labeled portion of the erythropoietin in the erythropoietin-erythropoietin binding complex is challenged with nonlabeled cold erythropoietin and the amount of the label is measured, labeled erythropoietin must be displaced with such cold erythropoietin.

Human erythropoietin is an acidic glycoprotein with an estimated molecular weight of 34,000. To prove the existence of the binding protein which specifically binds to erythropoietin, the studies were directed to show that erythropoietin and erythropoietin binding protein form the complex, that such complex has a higher molecular weight than erythropoietin alone and that the labeled erythropoietin can be displaced from the complex by using the cold nonlabeled erythropoietin.

Since the recombinant human erythropoietin is available and methods for its labeling are known, the existence of the erythropoietin-erythropoietin binding protein complex was shown by demonstrating the specific binding of the labeled and nonlabeled erythropoietin to the binding protein. Results of studies designed to show the existence of specific erythropoietin binding protein by proving the existence of the erythropoietin-erythropoietin binding protein complex having molecular weight higher than 34,000, are illustrated in FIGS. 1, 2A and 2B.

Gel filtration on Sephadex G-100 column was used to demonstrate the existence of erythropoietin binding protein. Normal human serum obtained either from normal volunteers or from Gibco (Gaithersburg, Md.) was used for experiments to demonstrate the existence and presence of erythropoietin binding protein in human serum. For these experiments, recombinant erythropoietin obtained from Genetics Institute, Boston, Mass. was iodinated using the chloramine-T method according to *Biochem. J.*, 89: 114 (1963) incorporated herein by reference. The average specific activity obtained by the iodination method was around 200 µCi/µg.

In a typical experiment, normal human serum was incubated with radiolabeled erythropoietin (~150,000 cpm) at 37° C. for about one hour and fractionated on a previously standardized Sephadex column at 4° C. Fractions (20 drops each) were collected. The radioactivity in the peak tubes which eluted either the free labeled erythropoietin or labeled erythropoietin bound to its binding protein were combined and concentrated to about 50–75 µl using Centricoh-30 filter, obtained from AMICON, Ltd., Beverly, Mass. Both concentrates were run separately on non-denaturing polyacrylamide gels for about four hours. Gels were stained with Rapid Coomassie Blue Stain, obtained from Diversified Biotech, Newton, Mass. Stained gels shown in FIG. 2A were dried and autoradiographed on Kodak X-Omat film (FIG. 2B).

FIG. 1 shows the elution profile of erythropoietin-erythropoietin binding protein complex, eluting as fraction 48, and free erythropoietin eluting as fraction 63.

The gel filtration on Sephadex was performed as follows: 10 µl of the $^{125}$I labeled erythropoietin was mixed with 2 ml of normal human serum previously centrifuged and filtered through 0.45 µ filters to remove particulates and incubated at 37° C. for about 1 hour. Samples of the human serum were divided into two groups. One group contained human serum mixed only with $^{125}$I-labeled erythropoietin containing approximately 100,000 cpm (—■—) (FIG. 1A). The second group contained the same components as the first group but additionally, 1 μg of cold unlabeled erythropoietin was added (—□—) (FIG. 1). Samples were then individually applied on Sephadex column (1.5×100 cm) and separated by gel filtration which separates proteins according to their size. The column was first precoated with albumin and calibrated with molecular markers. Markers used for column standardization were thyroglobulin (M.W. 670,000); bovine gamma globulin (M.W. 158,000); chicken ovalbumin (M.W. 44,000); horse myoglobin (M.W. 17,000); and cyanobalamin (M.W. 1,350). All markers were obtained and are available from BIO-RAD, Richmond, Calif. Markers were eluted with 50 mM phosphate buffer pH 7.5. Markers were eluted in 1 ml fractions and their absorbance at 280 nm determined by UV spectrophotometer. Fraction 48, later shown to elute erythropoietin-erythropoietin binding protein complex, had molecular weight close to fraction eluting bovine gamma globulin (M.W. 158,000). Fraction 63, later shown to elute free erythropoietin, was close to fraction eluting chicken ovalbumin, having M.W. 44,000. Samples 1 and 2 were separately applied on the Sephadex column and eluted using the same phosphate buffer at 4° C for about 4–5 hours.

As seen in FIG. 1, when the human serum was incubated with labeled $^{125}$I-erythropoietin, (A) the peak which eluted the primary fraction 48 was high, evidencing the presence of high amount of $^{125}$I-erythropoietin in the binding complex with erythropoietin binding protein. The second peak, eluting as a primary fraction 63, was smaller. When, however, 1 μg of nonlabeled cold erythropoietin was added to the human serum (B) containing the same amount of labeled $^{125}$I-erythropoietin, the radioactive erythropoietin was partially or completely displaced with such cold erythropoietin and moved to the free erythropoietin fraction 63. Such displacement shows that erythropoietin, whether labeled or cold, is bound to its binding protein forming the complex which elutes in the vicinity of the marker having M.W. 158,000. It further shows that the amount of the binding protein is a limiting factor in erythropoietin-erythropoietin binding protein complex. In any case, FIG. 1 clearly shows that there is the binding protein present which binds specifically to erythropoietin and forms the complex which has the molecular weight smaller than 158,000.

Gel filtration of normal human serum containing labeled erythropoietin was performed in the same fashion as described above.

It was subsequently confirmed that the peak corresponding to formed complex has 130,000 molecular weight and that it represents the complex formed between $^{125}$I-erythropoietin and its binding protein. When the excess of unlabeled cold erythropoietin was added, this erythropoietin competed with $^{125}$I-labeled erythropoietin for binding with binding protein. Consequently, the second sample seen in FIG. 1(Sample B) showed a much smaller peak of the complex than when the $^{125}$I-labeled erythropoietin was used solely. This finding confirms that there exists, in fact, the erythropoietin binding protein in normal human serum which binds exclusively to labeled or unlabeled erythropoietin. The displacement of $^{125}$I-labeled erythropoietin with unlabeled erythropoietin confirms the existence of such binding protein.

Total counts of $^{125}$I erythropoietin bound to the binding protein represented approximately 34–35% of total $^{125}$I-erythropoietin counts, with about 65–66% of labeled erythropoietin remaining and eluting as free erythropoietin.

To further confirm the presence of the binding protein complex obtained above from the normal human serum with labeled erythropoietin, the peak fractions were separated on the non-denaturing 7% polyacrylamide gel by electrophoresis. First, the appropriate fractions of the peaks containing erythropoietin-erythropoietin binding protein complex were pooled and concentrated to about 75 μl volume, using Centricon-30 inverse filter which has a molecular weight cut-off of 30,000. Similarly, the fractions corresponding to free labeled erythropoietin peak were concentrated to 50 μl.

Figure 2:
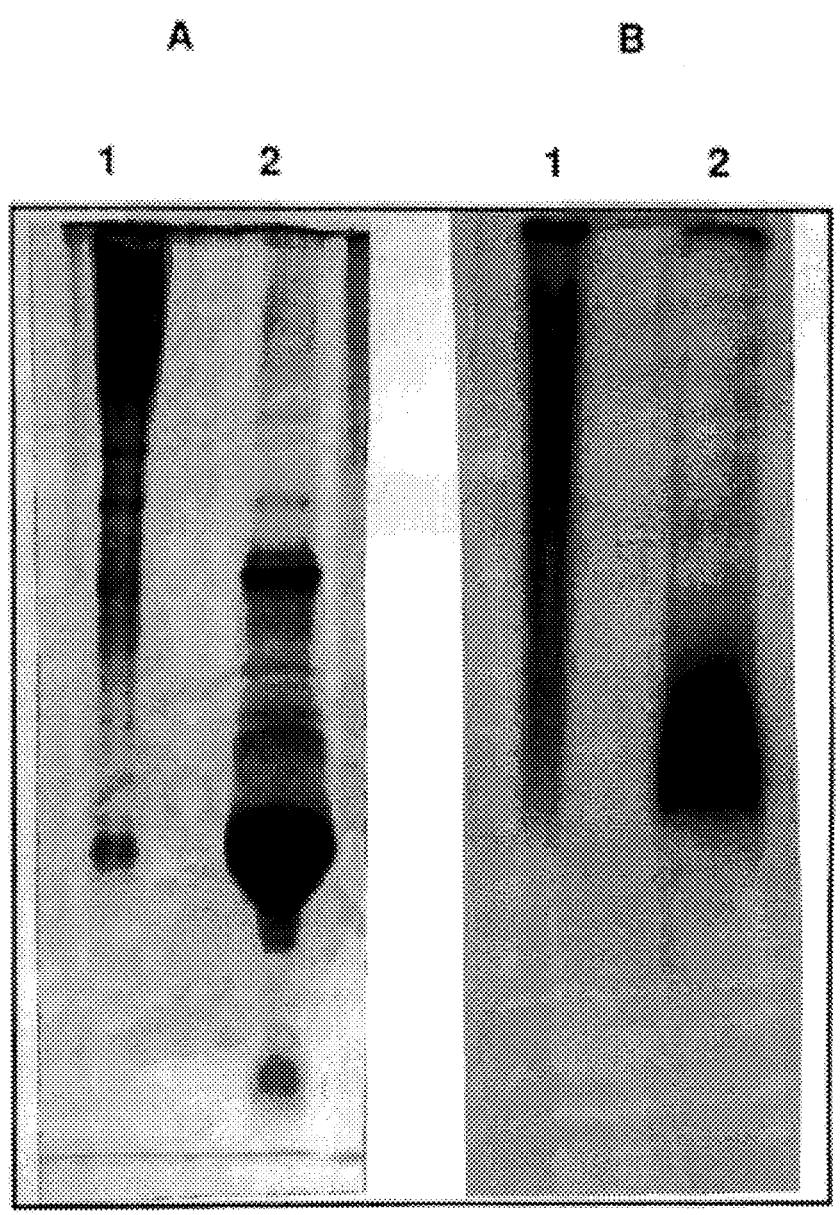
FIG. 2 shows (A) the concentrated binding protein complex (1) and free unbound labeled erythropoietin (2) on non-denaturing 7% polyacrylamide gel and (B) an autoradiograph showing a clear separation of concentrated erythropoietin binding protein complex and free unbound labeled erythropoietin.

Both concentrated fractions were run on non-denaturing polyacrylamide gels, as seen in FIG. 2 panel (A), wherein run 1 represents the concentrated fractions of eluted $^{125}$I-erythropoietin-erythropoietin binding protein complex and run 2 represents concentrated fractions of eluted $^{125}$I-erythropoietin. As seen in FIG. 2, (A), the two fractions have completely different separation pattern. The non-denaturing polyacrylamide gel electrophoresis is generally used for separation of a protein or protein complex without denaturation of protein complex. In FIG. 2, (A), there is a complete separation between runs 1 and 2, that is between free and erythropoietin and erythropoietin found in the complex.

Polyacrylamide gel electrophoresis—nondenaturing and discontinuous (PAGE-ND) method was obtained as a kit from Sigma Chemical Company and is described in detail in *Sigma Tech. Bull.*, No. EL-100, incorporated herein by reference. After PAGE-ND electrophoresis separation at constant current (50 mAmp) for four hours, the gels were stained with Rapid Coomassie Stain, obtained from Diversified Biotech, dried and autoradiographed on Kodak X-Omat film for about 24 hours, according to method described in *Basic Methods in Molecular Biology*, 331 (1986), Eds. L. Davis, M. D. Dibner and, J. F. Battey, Elsevier, N.Y. incorporated herein by reference. Results are shown in FIG. 2, panel (B). Lane 1 corresponds to run 1 in FIG. 2, (A), that is, it shows the radioactivity of the erythropoietin bound to the binding protein while the run 2 of the FIG. 2, (B) corresponds to free $^{125}$I-erythropoietin. Similarly to results seen in FIG. 2, (A), these two runs seen in panel (B) of FIG. 2 are very different. Run 1 clearly shows that the radioactivity is concentrated in a region corresponding to the erythropoietin-erythropoietin binding protein peak, while run 2 shows the radioactivity concentrated primarily in the labeled erythropoietin region.

Both FIGS. 1 and 2 clearly show that the binding protein exists and that such protein is able to bind specifically to a free erythropoietin and form the erythropoietin-erythropoietin protein complex.

II. Isolation of Erythropoietin-Erythropoietin Binding Protein Complex

Based on the above findings that the binding protein exists which specifically binds to erythropoietin, attempts were made to isolate the erythropoietin-erythropoietin binding protein complex.

Typically, such isolation was done by collecting binding protein complex peak obtained by using gel filtration, as described above, from normal human serum, by determining a total protein recovery and separating the concentrated fraction containing erythropoietin- erythropoietin binding protein complex on non-denaturing polyacrylamide gels. After separation, representative samples were stained for identification of the respective bands, regions of interest were cut out form the unstained gels, eluted, concentrated, incubated with labeled erythropoietin and re-electrophoresed on non-denaturing gels. Gels were dried, stained, and autoradiographed as described above.

Figure 3:
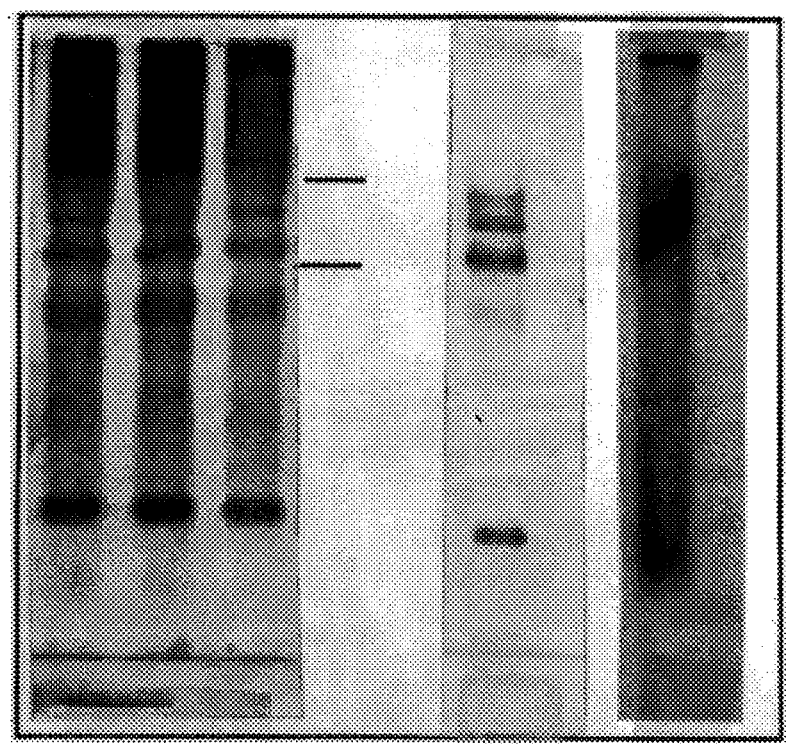
FIG. 3 shows (lane A) separation of gel filtration fractions corresponding to erythropoietin binding protein complex on non-denaturing polyacrylamide gel; (lane B) with respective bands of the gel cut out, eluted, concentrated and incubated with labeled erythropoietin on non-denaturing polyacrylamide gel; and (lane C) autoradiograph of the complex.

Results are demonstrated in FIG. 3. FIG. 3 (lanes A) represents separation of nonradioactive binding protein complex separated on non-denaturing polyacrylamide gel. For this study, five ml of normal human serum without labeled erythropoietin in 1 ml aliquots were fractionated on a Sephadex G-100 column (1.5×100 cm). The fractions containing the binding protein were pooled and concentrated to 5 ml. The total protein recovered was 140 mg, i.e., 28 mg/ml. Appropriate aliquot corresponding to 70 µg/per lane of protein was applied to 7% non-denaturing polyacrylamide gels, 10 lanes per gel.

A representative sample of three lanes was stained with Commassie Brilliant Blue Stain for the identification of the respective bands. These three lanes, stained are shown in FIG. 3 (lanes A), with a region of interest, based on results obtained in FIG. 2(A), identified and cut from the unstained gels. The cuts were minced with a razor blade, eluted in 2 ml distilled water overnight at 4° C., and concentrated to 200 µl on AMICON Centricon-30 filter having cut-off molecular weight of 30,000.

Sixty microliters of this concentrate were incubated with labeled erythropoietin containing approximately 40,000 cpm, for 1 hour at 37° C., and re-electrophoresed on 7% polyacrylamide non-denaturing gels. The results are shown in FIG. 3, lane B, wherein the region of interest taken from three gels in lanes A of FIG. 3 was further separated into several fractions. Since there is a labeled erythropoietin added, the gel with separated fractions was submitted to autoradiography, as seen in FIG. 3 (lane C). FIG. 3 clearly shows two regions where the radioactivity is concentrated to correspond to free labeled erythropoietin to bound labeled erythropoietin.

Figure 4:
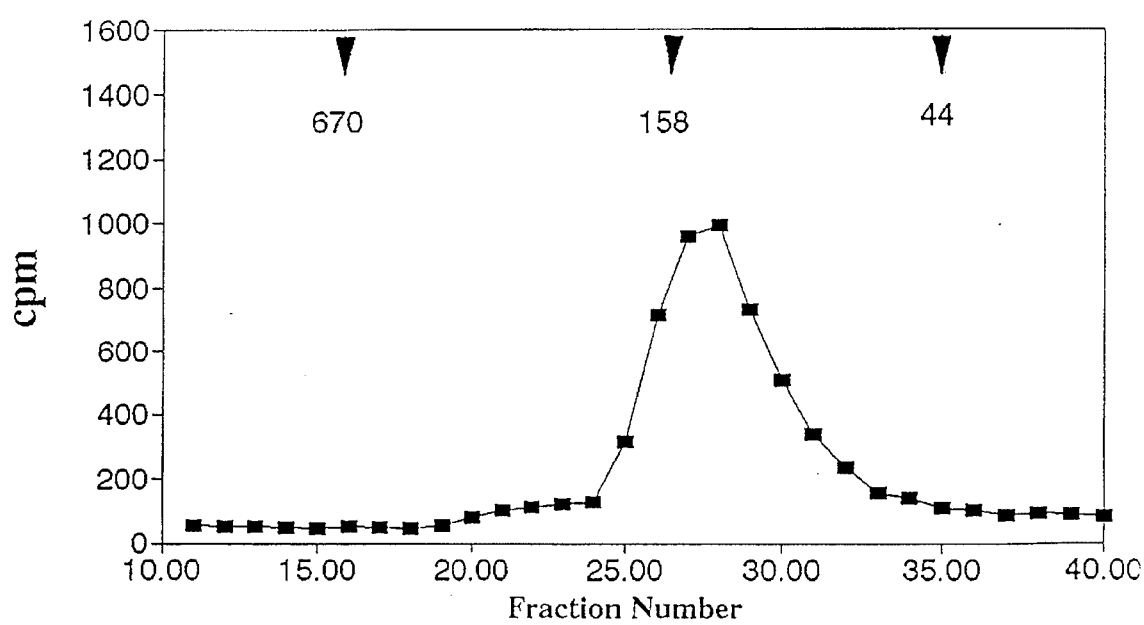
FIG. 4 depicts elution fraction peak of binding protein eluate, after incubation with labeled erythropoietin, from gel filtration using Sephacryl-S200.

To further confirm the molecular weight of the complex, 60 microliters of the above concentrate were incubated with 40,000 cpm for 1 hour at 37° C., and fractionated on Sephacryl-S200 column (1.5×30 cm) at room temperature. The column was eluted with a phosphate buffer described above. The elution pattern of labeled erythropoietin-erythropoietin binding complex is seen in FIG. 4, where the peak corresponding to the binding protein complex is eluted as fraction 26 and 27. The molecular weight of the complex was around 130,000 which was in agreement with prior findings.

III. Isolation and Separation of Binding Protein

When the erythropoietin-erythropoietin binding protein complex was isolated and its molecular weight determined to be around 130,000, it became apparent that the binding protein alone must have a molecular weight around 96,000, since the molecular weight of erythropoietin is 34,000.

One ml fractions were collected, absorbance measured and results were plotted against the standard curve previously constructed from the data obtained by unlabeled markers. FIG. 4 shows an elution pattern of the sample containing $^{125}$I-labeled erythropoietin. The primary peak is eluted in fractions 27 and 28. When the fraction 28 was read against the calibration curve from molecular markers, the molecular weight of the fraction 28 was determined to be around 130,000. Since the molecular weight of erythropoietin is around 34,000 and the protein eluted in fraction 28 had approximate molecular weight of 130,000, the protein which was bound to the $^{125}$I-labeled erythropoietin, had to have a molecular weight around 96,000 kDa. Therefore, the erythropoietin binding protein has a molecular weight of approximately 93,000-96,000.

To further confirm this finding, the studies were designed to utilize denaturing SDS polyacrylamide analysis of unlabeled erythropoietin-erythropoietin binding protein complex. Denaturing SDS polyacrylamide gel electrophoresis separates proteins, protein mixtures or complexes into monomeric proteins and determines their molecular weights. The molecular weight of a given protein is determined by comparing its relative mobility with those of known proteins. Denaturing polyacrylamide gel (PAGE-D) kit has been obtained from Sigma Chemical Company, St. Louis, Mo., as PAGE-D D kit and is described in *Technical Bulletin*, No. E1-2 and in *Nature*, 227: 680 (1970) (LAEMMLI), incorporated herein by reference.

The remaining concentrate (60 µl) from the experiments described above containing nonlabeled erythropoietin-erythropoietin binding protein complex was subjected to denaturing SDS polyacrylamide analysis using the Sigma "PAGE-D" kit. The concentrate and molecular weight standards were diluted 1:2 in sample denaturing buffer which lyses the protein complex into its protein components, and boiled for 15 minutes before loading the lanes either with the markers, as seen in FIG. 5 lane A, or with the sample as seen in lane B.

As the molecular weight markers, phosphorylase (b), (M.W. 97.4), bovine serum albumin (M.W. 69,000); ovalbumin (46,000); carbonic anhydrase (M.W. 30,000); trypsin inhibitor (M.W. 21.5) and lysozyme (M.W. 14,300) were used.

When run on a "PAGE-D" gel, markers provided clear separation pattern according to their molecular weights. Since the expected molecular weight of erythropoietin binding protein was in the vicinity of 96,000, phosphorylase having molecular weight 97,400 was used as the standard having highest molecular weight.

Figure 5:
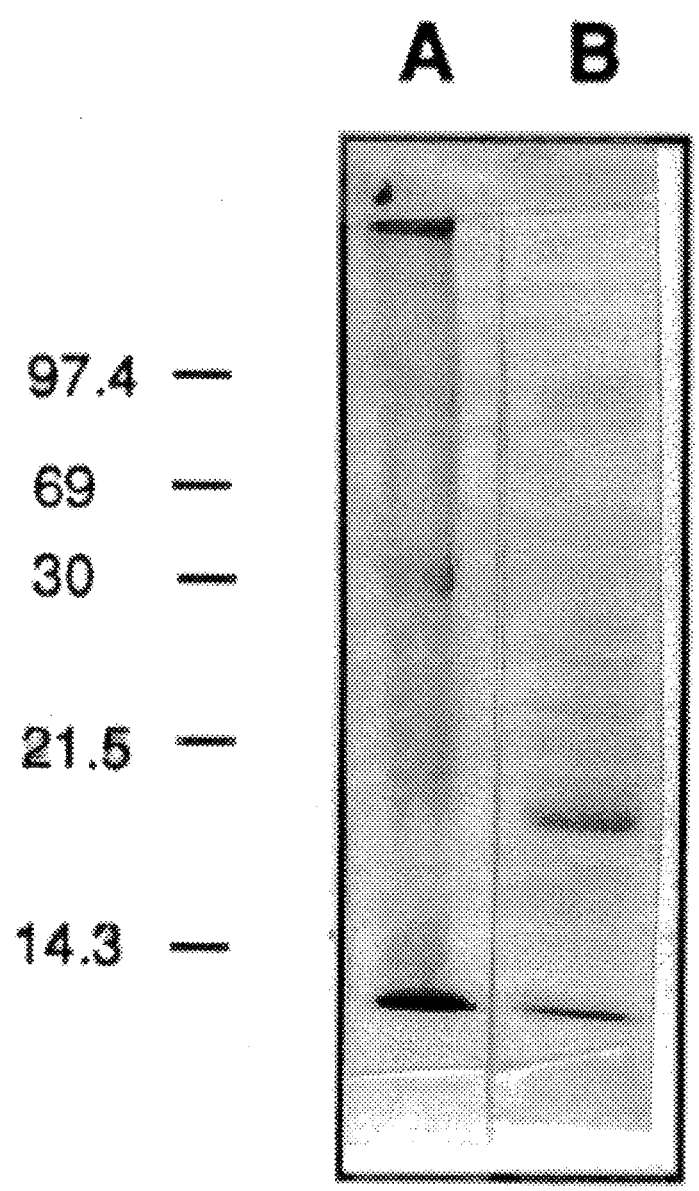
FIG. 5 is a denaturing SDS polyacrylamide gel of molecular markers (lane A) and erythropoietin binding protein (lane B).

FIG. 5 shows the separation of the molecular standards (lane A) run alongside of concentrate sample (lane B). FIG. 5 clearly shows that there is a fraction present which has only slightly lower molecular weight than the molecular weight marker phosphorylase (M.W. 97,400).

In this way, the existence, presence, and the molecular weight of the erythropoietin binding protein was confirmed.

IV. Confirmation of Presence of Binding Protein in Normal Human, Fetal, Newborn, and Anephric and Polycythemic Serum While the existence and presence of the binding protein in normal human serum was proven by above described studies, the confirmation experiments were performed to show whether the level of the binding protein would change depending on the physiological or pathophysiological status of the patient.

For this purpose, levels of the erythropoietin- erythropoietin binding protein complex was determined in normal human serum of healthy adult volunteers, in adult anephric patients, in adult polycythemic patients, and in serum from a fetus and from a newborn sheep. Representative results for each group are shown in FIGS. 6–10. The endogenous levels of erythropoietin were determined by radioimmunoassay (RIA), as described in *Recent Advances in Nuclear Medicine*, 6: 19–40 (1983) Ed. J. H. Lawrence and S. Winchell, Grune Shatton, Inc and incorporated herein by reference. The levels of binding protein were determined by gel filtration from the measurement of the labeled erythropoietin bound to the binding protein. The level of the binding protein is expressed in percent of binding of the binding protein to the radiolabeled erythropoietin based on measured cpm.

For the purposes of FIGS. 6–10, 0.5 ml of the serum was centrifuged and filtered through 0.45µ filters from Millipore to remove impurities, particulate matter and to assure that binding protein remains soluble in the filtrate. To each sample was added approximately 180,000 cpm of labeled erythropoietin and samples were incubated for 1 hour at 37° C. and at 4° C. overnight. Samples were then submitted to gel filtration, using Ultrogel ACA-44 column (1.5×100 cm), obtained from Biotechnics, N.J. The column was eluted with phosphate buffer containing 0.01% bovine serum albumin for 5 hours at 4° C. and 20 drops fractions were collected and the radioactivity measured.

Figure 6:
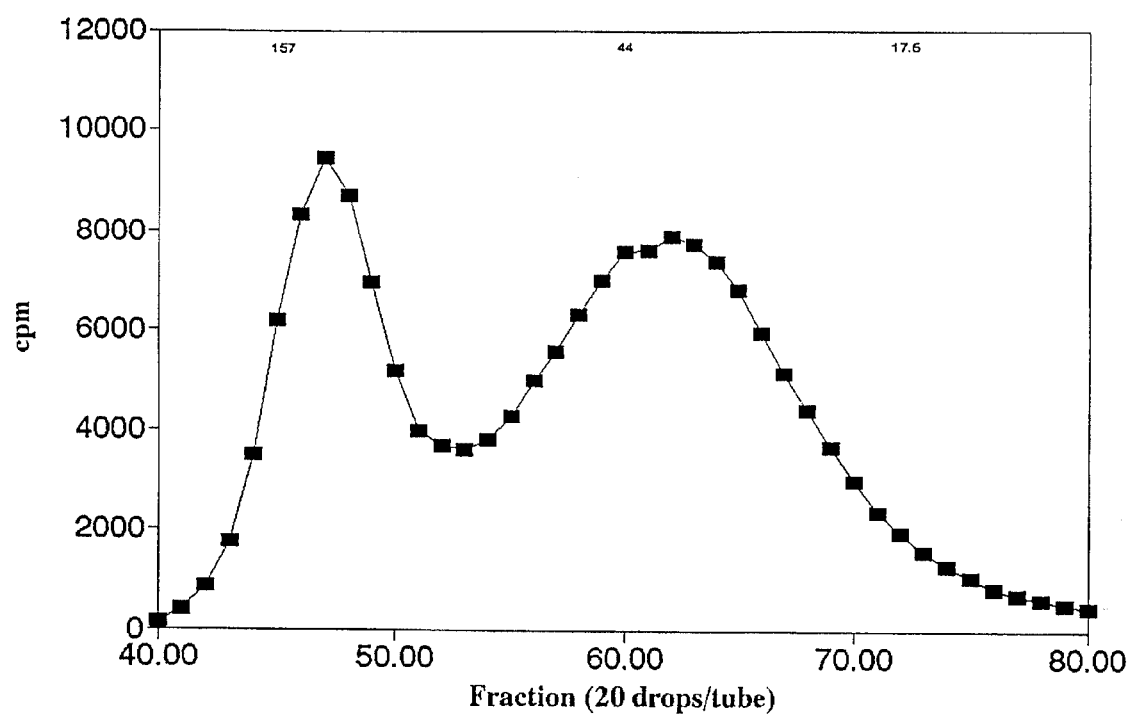
FIG. 6 depicts elution fraction peaks corresponding to the erythropoietin-erythropoietin binding protein complex and to a labeled free erythropoietin from the normal human serum.

FIG. 6 shows the elution pattern of binding protein peak eluting at fraction 48 and the free erythropoietin fraction eluting at fraction 62. In this set-up, the binding protein peak showed 35.1% of binding with the total erythropoietin present in 16.8 mU/ml, as determined by RIA.

Figure 7:
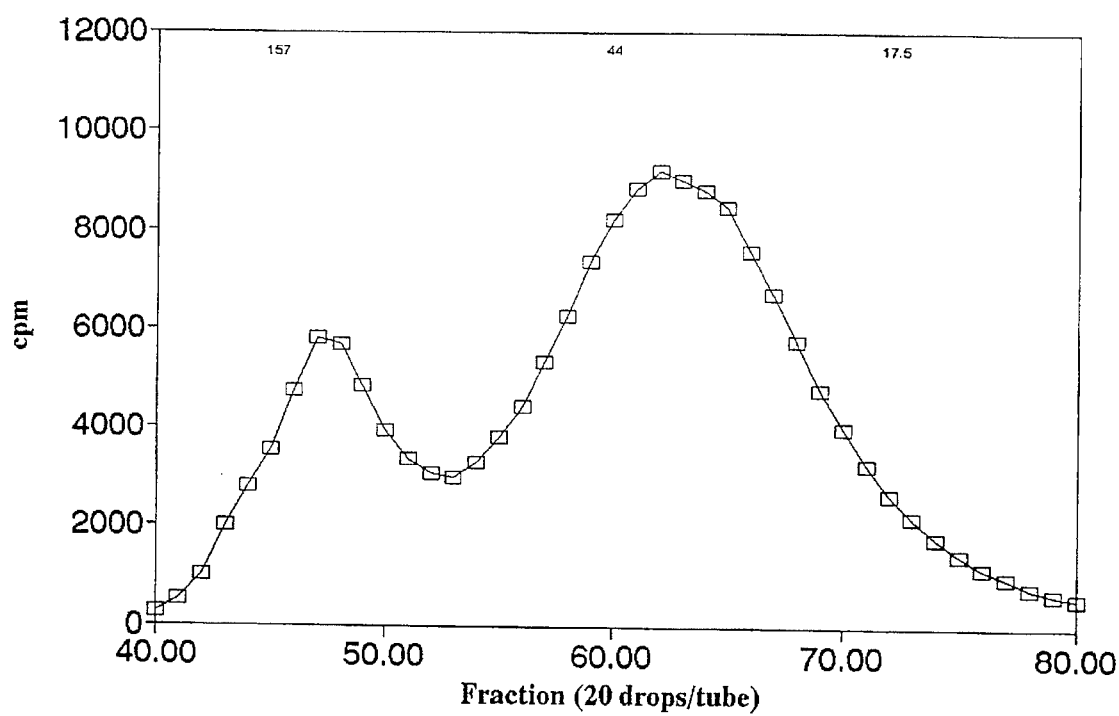
FIG. 7 depicts elution fraction peaks corresponding to the erythropoietin-erythropoietin binding protein complex and to a labeled free erythropoietin from the human fetal plasma.

FIG. 7 shows results obtained in human fetal plasma. The binding protein peak showed 23.4% of binding and the total erythropoietin present in amount 18.3 mU/ml, as determined by RIA. These findings are in agreement with prior knowledge that fetus has reduced concentrations of erythropoietin binding protein. Even though the circulating erythropoietin levels may be similar to adults, the biological efficacy of the endogenous erythropoietin is compromised and subject to more rapid metabolism; with a lesser amount of erythropoietin bound to erythropoietin binding protein, the half-life of fetal erythropoietin is short.

Figure 8:
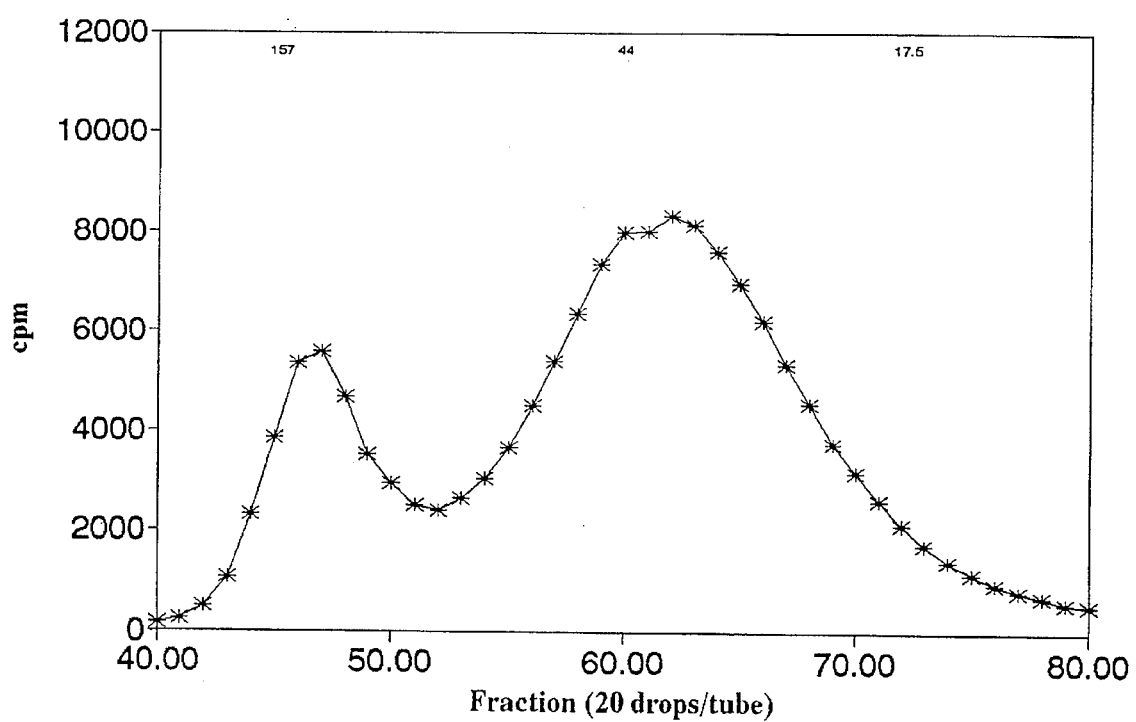
FIG. 8 depicts elution fraction peaks corresponding to the erythropoietin-erythropoietin binding protein complex and to a labeled free erythropoietin in a newborn sheep.

FIG. 8 shows the results obtained in the serum of the newborn sheep. The binding protein peak showed 23.3% of binding and the total level of erythropoietin was 9.0 mU/ml, as determined by RIA. As seen in FIG. 8, the level of erythropoietin in newborn is only about half of that of normal healthy adult and also of the fetus. At the time of birth, the kidneys take over and is become fully responsible for the production of erythropoietin. However, the level of binding protein is almost identical to that of the fetus, confirming that binding protein levels in newborns are similarly as low as in the fetus.

Figure 9:
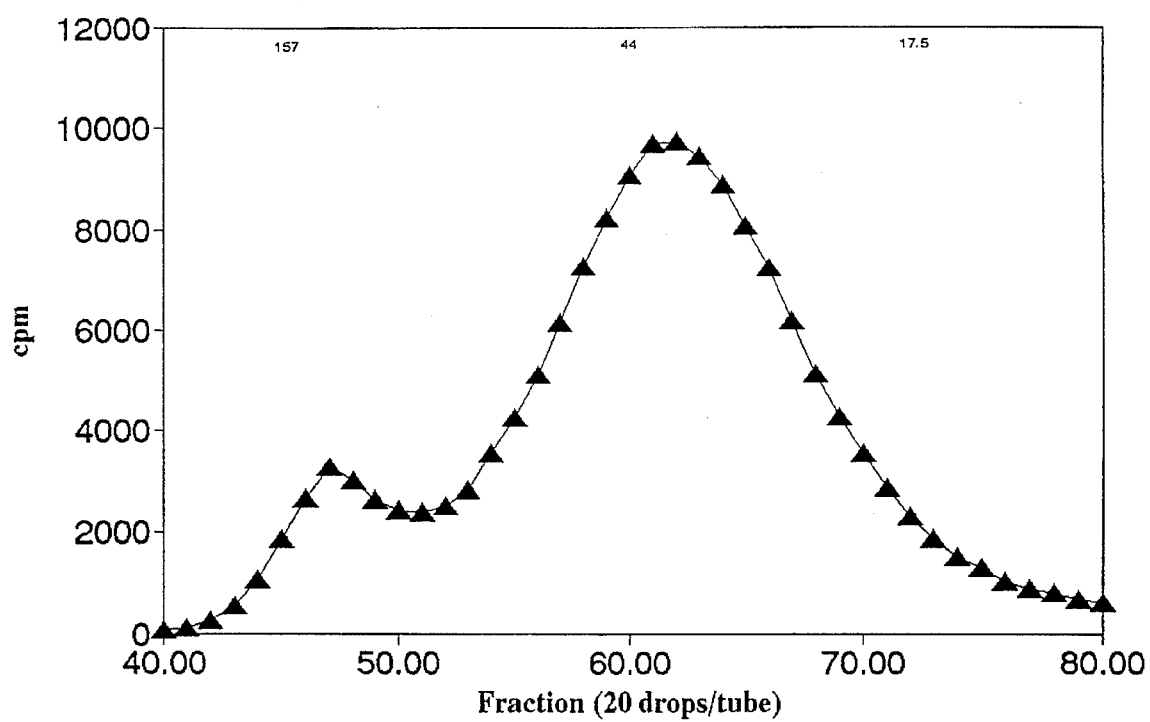
FIG. 9 depicts elution fraction peaks corresponding to the erythropoietin-erythropoietin binding protein complex and to a labeled free erythropoietin in serum of anephric patient.

FIG. 9 shows the results obtained in the serum of anephric patient. Since the anephric patient has no kidney or the function of the kidneys is severely limited or almost completely stopped, there is only very low level (7.7 mU/ml) of erythropoietin present in the anephric patients' serum. At the same time, the level of the binding protein is also very low of only 13.1%, that is about one-third of that of normal adult. The concentrations of erythropoietin binding protein in anephric or uremic patients, although low, may vary among patients and thus account for the fact that some patients require higher doses of human recombinant erythropoietin for the same correction of the hematocrit.

Figure 10:
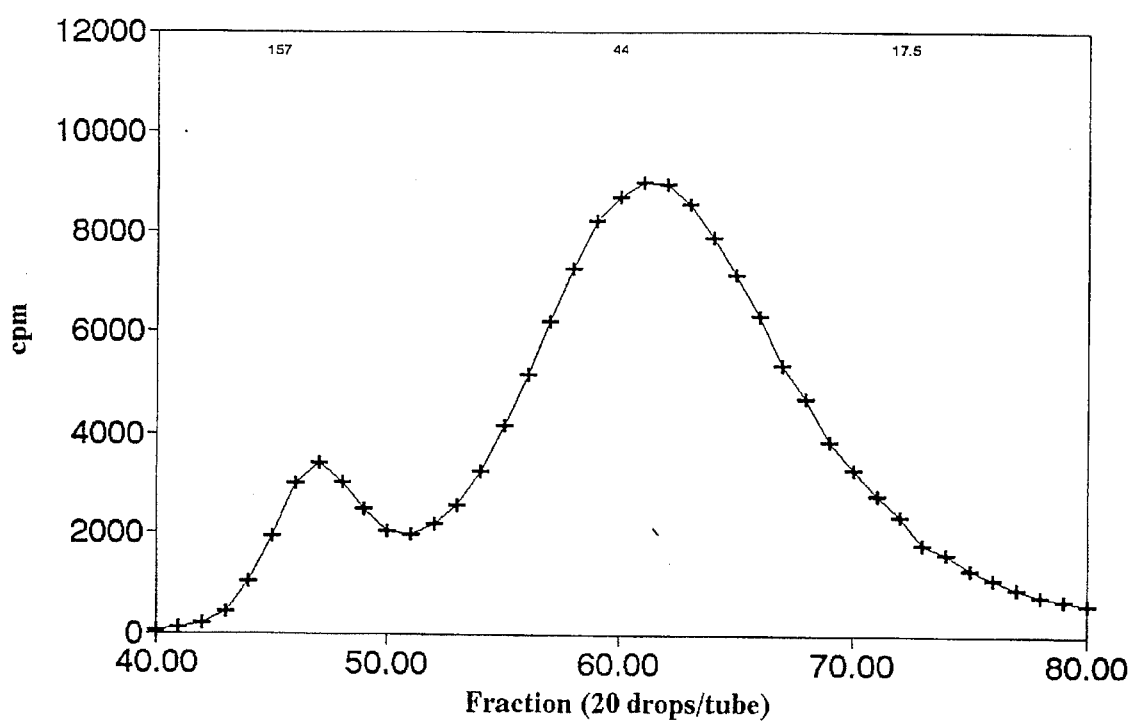
FIG. 10 depicts elution fraction peaks corresponding to the erythropoietin-erythropoietin binding protein complex and to a labeled free erythropoietin in serum of the patient suffering from secondary polycythemia.

FIG. 10 shows the results obtained in the serum of polycythemic patients. As seen from the curve, in these patients erythropoietin was present in large quantities (138 mU/ml) while the binding protein level was only 13.4%. Secondary polycythemia is characterized by elevated or high erythropoietin levels as measured by RIA. At higher than normal erythropoietin levels, the bound fraction progressively declines due to partial saturation of the binding protein by endogenous erythropoietin.

Comparison of individual levels of erythropoietin in percent bound in binding protein peak is shown in Table 1.

TABLE 1

Immunoreactive Serum Erythropoietin and Percent Bound in Binding Protein Peak

|  | Epo (mU/ml) | % EPO in EPO binding protein complex peak (%) |  |
|---|---|---|---|
|  | s.d. | s.d. |  |
| Normal Human Serum | 11.6 ± 3.3 | 35.0 ± 2.6 | n = 5 |
| Anephric Human Serum | 7.7 | 13.1 |  |
| Secondary Polycythemia | 138.0 | 13.4 |  |
| Human Fetal Plasma | 23.3 ± 5.0 | 24.7 ± 1.8 | n = 2 |
| Newborn Sheep Serum | 9.0 | 23.3 |  |

Table 1 shows that normal human serum has relatively high levels of erythropoietin bound to its binding protein. In pathological states, particularly in anephric patients, there is a very low level of immunoreactive erythropoietin and the label bound to the binding protein is only one third when compared to normals. In early life, whether in fetal or newborn plasma, the binding protein tends to be higher than in serum from anephric patients but it is still significantly lower than that found in normal human serum.

V. Determination of Specificity of Binding of Erythropoietin and Erythropoietin Binding Protein While the existence of erythropoietin binding protein was determined and its binding to erythropoietin and formation of erythropoietin-erythropoietin binding protein complex shown, the binding specificity was not altogether proven. In order to show that the newly discovered binding protein binds exclusively and selectively to erythropoietin, the same studies as described above for human serum were used. Additionally, however, unlabeled recombinant human growth hormone (5 µg) obtained from Genentech, S. San Francisco, Calif., was added to the normal human serum. The serum was mixed with labeled erythropoietin, gel filtrated and the radioactivity of the eluted fractions were determined.

Figure 11:
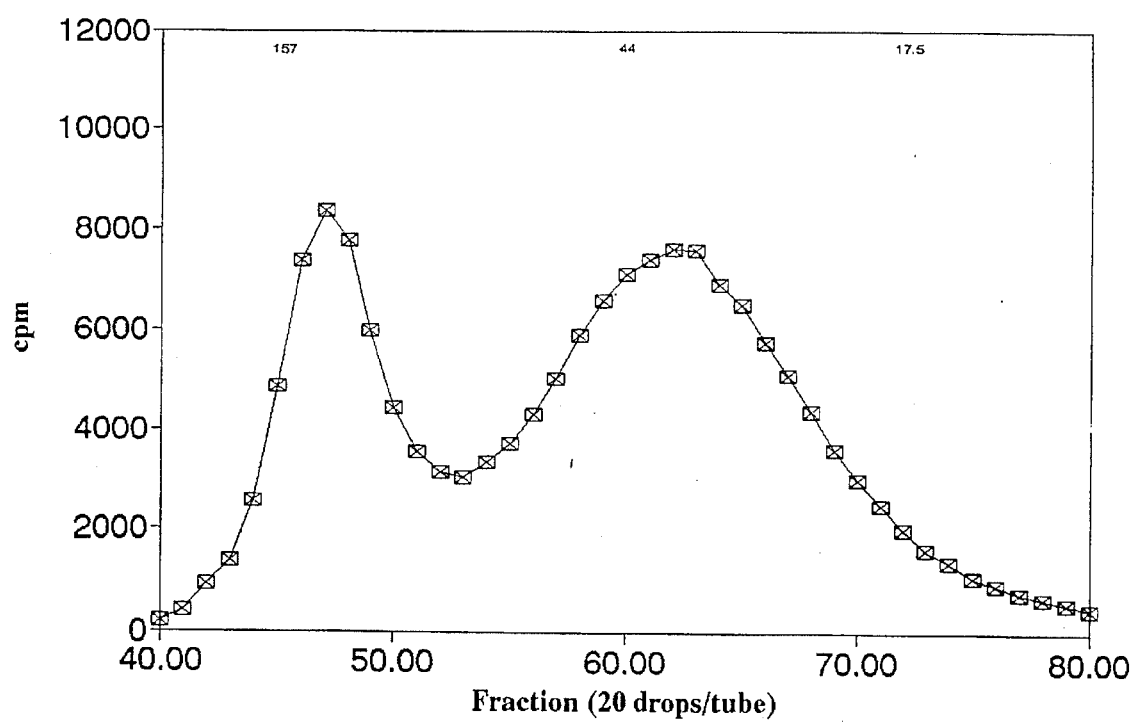
FIG. 11 shows the elution profile erythropoietin-erythropoietin binding protein complex and of free erythropoietin from the normal human plasma containing recombinant human growth hormone.

FIG. 11 illustrates the obtained results. Similarly to prior findings, as seen in FIG. 6 depicting the erythropoietin-erythropoietin binding protein complex peak in normal human serum, under the same conditions, the same results were observed for the serum additionally containing the growth hormone. The binding protein peak of the serum containing the growth hormone was the same and not lower than that observed in normal human serum showing that the binding protein did not bind to the growth hormone but it bound selectively to the labeled erythropoietin.

Thus, not only the existence, presence, and molecular weight but also the specificity of the newly discovered binding protein was unequivocally shown. If there would be present some nonspecific binding between the binding protein and growth hormone, a displacement of the labeled erythropoietin in the erythropoietin-erythropoietin binding protein complex peak would have been observed and the free erythropoietin peak would have increased due to the larger level of free erythropoietin.

VI. Purification of Erythropoietin Binding Protein

In order to provide the binding protein which could be used for its cloning and expression, erythropoietin binding protein was purified using generally method described in Biochem J., 221: 617 (1984), incorporated hereby by reference. The method utilizes affinity chromatography for selective purification on a erythropoietin—Affigel 15 affinity column. The technique is described in detail in Example 4. The purification of binding protein using method described in Example 4 resulted in 200–300 fold purification of the binding protein with no substantial change in binding affinity.

VII. Sequencing, Cloning and Expression of Erythropoietin Binding Protein

Following the purification of erythropoietin binding protein, protein is sequenced and cloned by methods known in the art. Isolated and purified binding protein is cloned according to methods for cloning and production of recombinant erythropoietin previously described in *Proc. Natl. Acad. Sci.*, 82: 7580 (1985) and in *Endocrine Genes*, 201–217 (1988), Ed. Yun-Fai Lau, Oxford University Press, N.Y. incorporated herein by reference.

Purified binding protein is used for sequence information, cloning and expression. Mixed oligodeoxyribonucleotide is designed containing all possible coding sequences for selected oligopeptide fragments. A human genomic library is screened for the probes. The isolated human genomic clone containing the binding protein is expressed in a SV 40 promoter-containing plasmid vector. Chinese hamster ovary cells are transfected with the expression vector and direct the production of the erythropoietin binding protein. The binding protein production is monitored by radioimmunoassay.

VIII. Development of Radioimmunoassay For Erythropoietin Binding Protein

The extent of erythropoietin bound to the binding protein under physiological conditions can be determined. Procedures to demonstrate the presence of erythropoietin binding protein and to separate erythropoietin binding protein free from bound erythropoietin by gel filtration can result in disruption of the binding equilibrium. Therefore, care must be taken to avoid underestimating the bound fraction.

The most reliable way to measure the concentrations of the binding protein in health and disease requires a direct chemical assay for the binding protein. Among the chemical assays developed for proteins, the radioimmunoassay offers the highest sensitivity, specificity and accuracy.

The essential requirements for the development of a radioimmunoassay (RIA) are: 1) specific antibodies to the protein under investigation, 2) the availability of the protein as pure as possible and its ability to accept radioactive label, 3) a standard reference preparation, and 4) a technique to separate the antibody-bound and non-antibody-bound protein.

Radioimmunoassay which can be developed for determination of the presence of erythropoietin binding protein is described in Example 5.

UTILITY

This invention concerns a newly discovered protein which specifically binds to erythropoietin, forming erythropoietin-erythropoietin binding protein complex. The function of erythropoietin on the erythropoiesis is well known. However, erythropoietin has relatively a short half-life, and therefore, in the absence of some mechanism to extend it, very large amounts of erythropoietin would have to be synthesized to meet the increased demand. It has now been shown that the half-life of erythropoietin is extended by forming a complex with its binding protein.

The formed complex extends the half-life of circulating erythropoietin and in this way, it effects erythropoiesis. The erythropoietin binding protein provides therefore an additional useful treatment for various types of anemias, particularly those which result from inability of the individual to produce its own erythropoietin. In instances where for any reason the synthesis of erythropoietin is decreased or insufficient, the administration of recombinant binding protein would substantially extend its half-life. While these anemias can be successfully treated with recombinant human erythropoietin, the dosages which are required in anephric patients or in prematurely born infants may be reduced when administered in combination with the erythropoietin binding protein.

By providing recombinant human erythropoietin in combination with its own recombinant or purified human binding protein, the half-life of circulating erythropoietin is substantially extended making the treatment with recombinant human erythropoietin more affordable and practical. Moreover, in patients not suffering from kidney diseases, but having for any reason a low count of red blood cells caused by low level of erythropoietin, the treatment with erythropoietin binding protein is sufficient to extend the half-life of erythropoietin and the erythropoiesis proceeds as if a normal level of erythropoietin is present.

The binding protein affects the homeostasis of erythropoietin and presumably the action of erythropoietin by altering its in vivo kinetics and metabolism and by modulating its interaction with tissue receptors. Therefore, changes in binding protein levels or activity may influence the ultimate expression of the biological activity of erythropoietin.

The binding protein is administered to a patient intravenously or subcutaneously in therapeutically effective doses which correspond to weight, age, blood circulation volume, affliction and the degree of affliction to be treated. Therapeutically effective doses are doses which are able to extend the half-life of erythropoietin from 6–8 hours to 9 hours and above, and to maintain the level of erythropoietin at such a level that it assures hematocrit above 25% and preferably around 40–47%. Doses of recombinant human erythropoietin needed to maintain such a level of hematocrit in anemic patients vary between 50 U/kg to 1500 U/kg of body weight and are given daily, every second day or biweekly. The therapeutically effective dosages of the recombinant human erythropoietin binding protein are between 10 U/kg to 1000 U/kg of weight in proportion to the degree of anemia and to the dose of erythropoietin needed to correct the hematocrit. Recombinant human erythropoietin binding protein is administered alone or in combination as a complex with recombinant erythropoietin. The complex or the binding protein alone are given therapeutically as well as prophylactically for treatment of anemia, before or after surgery or during any extended bleeding.

EXAMPLE 1

Demonstration of Existence of Specific Binding Protein for Erythropoietin in Normal Human Serum This example describes the studies which demonstrate the existence of the binding protein for hormone erythropoietin in normal human serum.

A normal human serum pool was obtained from Gibco Co. as product no. 200–6150 PG or Y3N 7802.

Labeled erythropoietin was prepared by iodination, by chloramine-T method, according to *Biochem J.*, 89: 114

(1963) incorporated herein by reference, of recombinant erythropoietin or erythropoietin extracted from the urine of anemic patients. Each vial for iodination contained approximately 0.7 μg of lyophilized erythropoietin, or about 57 units (U). Lyophilized erythropoietin was dissolved in 20 μl of 0.5M phosphate buffer at pH 7.5, 20 μl of distilled water and 1 mCi of Na$^{125}$I in 3 μl were added to the vial containing dissolved erythropoietin. Then, 10 μl of chloramine-T (400 μg/ml) was added and the mixture was submitted to a mild agitation for 1 minute, 100 μl of metabisulfide (240 μg/ml) and 300 μl potassium iodine (100 μg/ml) were added. All three agents were prepared freshly in phosphate buffer (0.05M, pH 7.5) immediately before iodination. The total content of the vial was transferred to a small Sephadex G-25 column having a bed volume 10 ml, which was previously coated with bovine serum albumin (BSA) and eluted in 1 ml aliquots. The eluant was carefully monitored and protein bound $^{125}$I labeled protein was eluted as fraction 4, and unreacted free $^{125}$I label as fractions 8–10. The total content of $^{125}$I labeled protein was further fractionated on a 1.5×30 cm Sephadex G-150 column and eluted in 20 drops fractions with phosphate buffer (0.05M, pH 7.5). The second fractionation yielded two major peaks. The first peak contained damaged label or aggregation of the labeled hormone. The undamaged labeled hormone appeared as a second peak. Typically, the average specific activity of iodinated erythropoietin was 200 μCi/μg which was equivalent to approximately 200,000 cmp/10μl/5 mU erythropoietin.

One ml of normal human serum was incubated with 10 μl (200,000 cpm/5 mU) of erythropoietin for 1 hour at 37° C. After the incubation, samples were separated by gel filtration on Sephadex G-100 column. Samples were placed on the Sephadex G-100 (obtained from Pharmacia) column (1.5×100 cm) previously precoated with albumin and calibrated with molecular markers having molecular weights 670,000; 158,000; 44,000; 17,000; and 1,350, and eluted with 50 mM phosphate buffer pH 7.5. The gel filtration was performed at 4° C. and about 1 ml fractions corresponding to 20 drops of eluate were collected.

Gel chromatography resulted in three peaks separating bound and free hormone from the free iodine, as measured by the radioactivity in individual fractions. The first peak corresponded to a protein or protein complex having ~130,000 molecular weight and was identified as erythropoietin-erythropoietin binding protein complex having combined molecular weight of erythropoietin equal 34,000 kD and erythropoietin-erythropoietin binding protein complex equal to 96,000 kDa. FIG. 6 shows elution of the complex and free erythropoietin peak. The peak for unbound iodine is not shown. The first and the second peak fractions corresponding to the erythropoietin-erythropoietin binding protein complex and to free erythropoietin, respectively, were pooled and concentrated to about 50–75 μl in AMICON Centricoh-30 filter with a molecular weight cut-off of 30,000. The volume of the second EPO peak concentrate was adjusted to yield approximately the same level of radioactivity.

Both preparations were subjected to non-denaturing 7% polyacrylamide gel electrophoresis for 4 hours at 50 mAmp. After electrophoresis, the gel was placed into stain (0.1% Coomassie blue in 40% methanol and 10% acetic acid) for one hour. The gel was dried and autoradiographed for 24 hours and 96 hours using Kodak XAR film and DuPont intensifying screen. The autoradiograph showed a clear separation between specifically bound erythropoietin-erythropoietin binding protein complex and free unbound erythropoietin as seen in FIG. 2, A1 and A2.

EXAMPLE 2

Identification of Specific Binding Protein for Erythropoietin in Normal Human Serum This example describes how the erythropoietin binding protein was identified.

Five ml of normal human serum without labeled EPO in 1 ml aliquots were placed on the same type of Sephadex G-100 column, as used in Example 1, the same fractions were pooled and concentrated to about 5 ml of total volume, as described in Example 1. The total protein recovered was 140 mg, i.e. 28 mg/ml. Sixty microliters of this concentrate was incubated with 4 μl of labeled $^{125}$I-erythropoietin (40,000 cpm) in 100 μl of 0.5% bovine serum albumin for 1 hour at 37° C. The incubation mixture was applied on a column previously calibrated with same markers, as described in Example 1, of Sephacryl S-200 (1.6×28 cm) and gel was eluted for 5 hours at room temperature with phosphate buffer. Gel filtration resulted in a single peak of radioactivity at a position of ~130,000 M.W.

EXAMPLE 3

Binding of Erythropoietin Binding Protein to Erythropoietin

This example illustrates specific binding of the erythropoietin binding protein to erythropoietin.

The concentrate prepared as in Example 2 was incubated for 1 hour with 4 μl of labeled EPO having 100,000 cpm and subjected to non-denaturing electrophoresis on 7% polyacrylamide gel electrophoresis for 4 hours at 50 mAmp, as described in Example 1, followed by autoradiography. Autoradiography, under conditions described in Example 1, showed two identifiable bands which had specifically bound labeled EPO. These two bands were cut out and eluted in 50 mM phosphate buffer overnight. The eluate was concentrated and analyzed by electrophoresis on denaturing SDS-PAGE. After being combined with 2% sodium dodecyl sulphate and 100 mM dithiothreitol and boiled for 15 minutes, the samples were applied to vertical slab 7% polyacrylamide gels and run according to the method of Laemmli, Nature, 277: 680 (1970) incorporated herein by reference. The following markers were used: myosin (M.W. 200,000); phosphorylase (M.W. 97,400); bovine serum albumin (M.W. 69,000); ovalbumin (M.W. 46,000); carbonic anhydrase (M.W. 30,000); trypsin inhibitor (M.W. 21,500); and lysozyme (M.W. 14,500). One major band of the binding protein was determined to have a molecular weight of approximately 96,000. There were two minor bands with a molecular weight somewhat smaller.

EXAMPLE 4

Purification of Erythropoietin Binding Protein

This example illustrates purification of erythropoietin binding protein using human erythropoietin—Affigel 15.

Human erythropoietin (70 mg) was covalently linked to 17 g of Affigel 15 at pH 7.5 (0.1m-HEPES buffer) with gentle agitation for 1 hour at room temperature. Any free, active esters remaining on the gel were blocked with 1.2 ml of 7M-ethanolamine/HCl (pH 8). Approximately 91% of the human erythropoietin remained linked following thorough sequential washing with 25mM-Tris/HCl, pH 7.4, and 4M-MgCl$_2$, as determined by the inclusion of a small amount of $^{125}$I-human erythropoietin in the original reaction mixture. Erythropoietin binding protein prepared from 10 ml of normal human serum as in Example 2 (4 ml, 10–20 mg of protein/ml) was applied to a column (0.7 cm×25 cm) of human erythropoietin Affigel 15 and allowed to interact for 1 hour at 21°–22° C. The column was then washed with 25 mM Tris/HCl(pH 7.4) containing 40 mM-CaCl$_2$, 0.02% (w/v) NaN$_3$ and Trasylol (1000k-i.u./ml) and the bound serum protein(s) were eluted with 4M-urea and 4M-MgCl$_2$, either alone or sequentially as described in *J. Biol. Chem.*, 25: 6815 (1979) incorporated herein by reference. The bound fractions were dialyzed against 25mM-Tris/HCl, pH 7.5, containing 40mM-CaCl$_2$ and then assayed as above for $^{125}$I-binding. The yield is about 30–40%.

The purified erythropoietin binding protein is confirmed by SDS-PAGE to be a pure protein having a molecular weight 96,000.

EXAMPLE 5

Radioimmunoassay for Erythropoietin Binding Protein Antibody Production

This example illustrates a radioimmunoassay developed for production of erythropoietin binding protein antibody. The protocol for radioimmunoassay is essentially that which is described in *Recent Advances in Nuclear Medicine*, 6: 19 (1983) Ed. J. H. Lawrence, S. Winchell, Grune Shatton, Inc. incorporated herein by reference.

The binding protein for immunization is obtained as above. For use in the radioimmunoassay, the binding protein is submitted to two step purification. Normal human serum is fractionated by column chromatography, the appropriate fractions containing the binding protein are pooled, concentrated and subjected to non-denaturing polyacrylamide electrophoresis as described in Example 2. The regions previously identified as containing the binding protein are cut, minced and eluted overnight in distilled water. The eluate (0.1–0.5mg) is emulsified with an equal volume of Freund's complete adjuvant (Sigma, St. Louis, Mo.) and injected subcutaneously at multiple sites into the legs of young New Zealand white rabbits. Additional boosters are given at two week intervals for two months. The rabbits are bled from the central ear artery (50 ml) and the antiserum is evaluated.

In order to be useful for the RIA, the antiserum has to have a high titer, i.e., it must be able to be used at a high dilution (1:10,000), it has to be specific, i.e., not cross-react with other proteins, and have a high affinity to the binding protein. In order for this RIA to measure the binding protein only, and not the erythropoietin-erythropoietin binding protein complex, the required affinity of the erythropoietin to antiserum has to be higher than the affinity of the binding protein to erythropoietin. This is not difficult to do because antisera in general have higher affinities than binding characteristics under physiological conditions.

Binding Protein For Labeling

The eluate from the two step purification procedure above is further purified on an erythropoietin-affinity column as described in Example 4. After this step the binding protein is pure enough for radioiodination using chloramine-T method. For each iodination 1 ug of protein is needed.

The same preparation of purified erythropoietin binding protein as described above is used for the standard preparation in the radioimmunoassay. Based on serum binding protein concentrations of 300 picograms/ml in normal humans, dilutions of the standard is such that normal values fell in the middle part of the standard curve. It is so specifically designed in order to allow the measurement of reduced and increased binding protein concentrations in various erythropoietic states. Serial dilutions of the standard curve is in the range from 2 nanograms/ml to 2 picograms/ml. The separation of the bound binding protein (or antibody) from free binding protein is done by double antiserum technique utilizing the precipitation of the antibody-analyte complex by a second antiserum, an anti-gamma globulin. The first antibody is a rabbit antiserum produced against human erythropoietin binding protein. The antiserum produced in goats against rabbit gamma globulin facilitates the precipitation of the primary antibody binding protein complex.

Samples of 100 μl of undiluted or diluted human serum are pipetted into polystyrene tubes (12×75 mm). The diluent buffer is phosphate buffer (0.05M, pH 7.5) containing 5% of human serum albumin. A volume of 200 μl of labeled erythropoietin binding protein and 200 μl of erythropoietin binding protein antiserum are added simultaneously. The labeled erythropoietin binding protein is diluted to contain approximately 10,000 cpm/200 μl. The antiserum (200 μl) dilution of 1:20,000, is such that it bound approximately 35–40% of the label. The reaction mixture is incubated for 4 days at 4° C. The separation of the antibody bound labeled erythropoietin binding protein is accomplished with a goat anti-rabbit gamma globulin antiserum (400 μl) plus normal rabbit serum (100 μl) used as a carrier.

EXAMPLE 6

Diagnostic Radioimmunoassay Kit

This example describes the diagnostic radioimmunoassay kit for the quantitative measurement of human erythropoietin binding protein in serum.

The erythropoietin double antibody radioimmunoassay kit is intended for the quantitative measurement of erythropoietin binding protein in serum as an aid in the diagnosis and treatment manipulation of anemias and polycythemias. This assay is intended for in vitro diagnostic use.

The procedure follows the basic principle of radioimmunoassay whereby there is competition between a radioactive and nonradioactive antigen for a fixed number of antibody binding sites. The amount of 125I labeled erythropoietin binding protein bound to the antibody is inversely proportional to the concentration of erythropoietin binding protein present in the serum. The separation of free and bound antigen is easily and rapidly achieved by using an accelerated double antibody polyethylene glycol system.

Lyophilized erythropoietin binding protein standard are prepared containing approximately concentrations of 0, 75, 150, 300, 600, and 1000 pg/ml of purified erythropoietin binding protein from human serum in a protein based buffer.

$^{125}$I labeled erythropoietin binding protein is prepared, as described above.

Rabbit anti-human serum erythropoietin binding protein is prepared as described in Example 5.

Good anti-rabbit gamma globulin serum using polyethylene glycol as a precipitating aid is prepared.

Procedure:

Specimen serum is obtained by venipuncture. The serum may be stored at 2°–8° C. for up to 24 hours and should be frozen at −10° C. or lower for longer periods.

All reagents are used at room temperature (15°–30° C.) and mixed thoroughly before using. Standards, controls, and specimens are assayed in duplicate.

1. Test tubes, in duplicate, are labeled and arranged for total counts, non-specific binding, standards, controls and specimen samples.

2. 100 μl of the standards, controls or specimens are added to all tubes, except the total count and non-specific binding (NSB) tubes. To the NSB tubes, 200 μl of standard containing 0 mU/ml is added.

3. 100 μl of EPO-BP antiserum, is added to all tubes, except the Total Count and NSB tubes. All tubes are vortexed.

4. All tubes are incubated at 37° C. in a water bath for 4 hours.

5. 100 μl of $^{125}$I EPO-Bp reagent is added to all tubes.

6. Tubes are incubated at room temperature for 16–20 hours.

7. 1 ml of goat gamma anti-rabbit serum is added to all tubes except Total Count tubes.

8. Tubes are vortexed and incubated at room temperature for 30 minutes.

9. Tubes are centrifuged (except Total Count Tubes) for 15–20 minutes at 1500 x g.

10. The supernatant is decanted by inverting each tube or a rack of tubes (when tubes are firmly held). The tubes are inverted and allowed to drain for 15–20 seconds on absorbent paper. After draining, the mouth of each tube is blotted to remove any droplets adhering to the rim before returning the tubes upright.

11. All tubes are counted in a gamma counter for one minute.

12. Results are calculated for the average counts per minute (CPM) for each standard, patient sample, and control. The average of CPM of the NSB are subtracted from all counts to obtain corrected net counts. The % bound is calculated for each standard, patient sample, and control as follows:

$$\% \text{ Bound} = \frac{\text{Sample Counts} - \textit{NSB} \text{ Counts}}{\text{Average Total Counts}} \times 100$$

A curve of radioactivity counts per minute is plotted, % bound for the EPO standards against the EPO concentration on a linear-log graph paper. The EPO-BP concentration of specimen sample is determined from the standard curve.

What is claimed is:

1. A purified erythropoietin-binding protein, wherein said protein is obtainable from mammalian serum, has a molecular weight of from about 90 kDa to 100 kDa as determined by size exclusion chromatography, and is capable of specifically binding to mammalian erythropoietin.

2. A purified protein according to claim 1, wherein said molecular weight is from about 92 kDa to 97.4 kDa.

3. A purified protein according to claim 1, wherein said molecular weight is from about 93 kDa to 96 kDa.

4. A purified protein according to claim 1, modified by the addition of a detectable label.

5. A detectably labeled protein according to claim 4, wherein the label is selected from the group consisting of a fluorescent marker, an enzyme, a radioisotope, and an antibody.

6. A composition comprising a purified protein according to claim 1 and a pharmaceutically acceptable carrier.

7. A purified complex consisting of an erythropoietin-binding protein bound to erythropoietin, wherein said complex has a molecular weight of from about 125 kDa to 135 kDa as determined by size exclusion chromatography, and wherein said binding protein is obtainable from mammalian serum and specifically binds to said erythropoietin.

8. A purified complex according to claim 7, wherein said molecular weight is about 130 kDa.

* * * * *